United States Patent [19]

Reers et al.

[11] Patent Number: 5,571,784

[45] Date of Patent: Nov. 5, 1996

[54] USE OF VWF-CONTAINING CONCENTRATES AS A THERAPY WHICH IS EMPLOYED IN COMBINATION WITH ANTITHROMBOTIC AND FIBRINOLYTIC THERAPY

[75] Inventors: Martin Reers; Gerhard Dickneite, both of Marburg, Germany

[73] Assignee: Behringwerke Aktiengesellschaft, Marburg, Germany

[21] Appl. No.: 544,867

[22] Filed: Oct. 18, 1995

[30] Foreign Application Priority Data

Oct. 20, 1994 [DE] Germany .......................... 44 37 544.1

[51] Int. Cl.$^6$ ................................................. A61K 38/00
[52] U.S. Cl. ........................................................... 514/2
[58] Field of Search .................................. 424/10; 514/2

[56] References Cited

U.S. PATENT DOCUMENTS

| | | | |
|---|---|---|---|
| 4,774,323 | 9/1988 | Newman et al. | 530/383 |
| 5,112,950 | 5/1992 | Meulien et al. | 530/383 |
| 5,198,349 | 3/1993 | Kaufman | 530/383 |
| 5,200,510 | 4/1993 | Kumar et al. | 530/383 |
| 5,204,323 | 4/1993 | Findlay et al. | 514/2 |
| 5,366,869 | 11/1994 | Goldstein | 435/13 |
| 5,408,039 | 4/1995 | Burnouf-Radosevich et al. | 530/383 |

FOREIGN PATENT DOCUMENTS

| | | |
|---|---|---|
| 0367713B1 | 5/1990 | European Pat. Off. . |
| WO92/20361 | 11/1992 | WIPO . |

OTHER PUBLICATIONS

Tamao, Y. et al., "Effect of a Selective Thrombin Inhibitor MCI–9038 on Fibrinolysis In Vitro and In Vivo", Thrombosis and Haemostasis, 56(1):28–34(1986).

Mannucci, P. M. et al., "1–Deamino–8–D–Arginine Vasopressin: A New Pharmacological Approach to the Management of Haemophilia and Von Willebrand's Disease", The Lancet Ltd., pp. 869–872, (1977).

Lethagen, S. et al., "New Bleeding Time Devices With Retractable Blades Evaluated in Children, Healthy Volunteers and Patients With Prolonged Bleeding Time", Thrombosis and Haemostasis, 70(4):595–597(1993).

Ruggeri Z., "New Insights Into the Mechanisms of Platelet Adhesion and Aggregation", Seminars in Hematology, 31(3):229–239(1994).

Hemker H. C. et al., "Der Mechanismus der Hämostase", Theoretische Voraussetzungen, pp. 1–18, (1993).

Ruggeri, Z., "von Willebrand Factor and Fibrinogen", Current Opinion in Cell Biology, 5:898–906 (1993).

Alevriadou B. R. et al., "Real–Time Analysis of Shear–Dependent Thrombus Formation and Its Blockade by Inhibitors of von Willebrand Factor Binding to Platelets", Blood, 81(5):1263–1276 (1993).

Gralnick, H. R. et al., "A Monomeric von Willebrand Factor Fragment, Leu–504–Ser–728, Inhibits von Willebrand Factor Interaction With Glycoprotein Ib–IX", Proc. Natl. Acad. Sci., 89:7880–7884 (1992).

Primary Examiner—Raymond Henley, III
Attorney, Agent, or Firm—Finnegan, Henderson, Farabow, Garrett & Dunner, L.L.P.

[57] ABSTRACT

The invention relates to the administration of von Willebrand factor (vWF)-containing drugs in association with the therapeutic use of blood anticoagulants, either on their own or together with fibrinolytics. The administration, which is for the purpose of reducing the risk of hemorrhages in patients, can take place either at the same time or following the anticoagulant and lytic treatment. A therapy principle is described which separates, during therapy, the desirable effect of anticoagulation and/or fibrinolysis from the undesirable side effect of hemorrhagic tendency.

2 Claims, 1 Drawing Sheet

USE OF VWF-CONTAINING CONCENTRATES AS A THERAPY WHICH IS EMPLOYED IN COMBINATION WITH ANTITHROMBOTIC AND FIBRINOLYTIC THERAPY

The invention relates to the administration of von Willebrand factor (vWF)-containing drugs in association with the use of blood anticoagulants, either on their own or together with fibrinolytics, as a therapy. The administration, which is for the purpose of reducing the risk of hemorrhage in patients, can take place either at the same time as, or following, the anticoagulant and lyric treatment. A therapy principle is described which separates the desirable anticoagulant and/or fibrinolytic effect from the undesirable side effect of hemorrhagic tendency.

Imbalances in the components of coagulation and of fibrinolysis manifest themselves clinically in thrombophilia, on the one hand, and in hemorrhagic tendency, on the other. Both pathological conditions can have life-threatening consequences. In the case of thrombophilia, such as, for example, in association with acute myocardial infarction, attempts are made, in many instances, to regulate the prevailing imbalance in lysis and coagulation. For example, the fibrinolytic system is supported by administering streptokinase (SK) or plasminogen activators (t-PA or uPA, recombinant where appropriate) in order to dissolve any blood clot which is already present. The clotting system is either completely suppressed or else dampened down by means, for example, of heparin or low molecular weight heparin (LMWH), or by means of thrombin inhibitors, such as, for example, the synthetic inhibitor MCI-9038 (Tamao Y. et al. Thromb. Haemost. 56, 1, 28–34, 1987) or recombinant hirudin (r-Hir), or by means of factor Xa inhibitors such as recombinant tick anticoagulant protein (r-TAP), or by means of platelet antagonists such as aspirin or 7E3 antibodies directed against thrombocytes. This results in thrombotically occluded vessels being opened and in further thrombus formation being prevented. Nevertheless, a certain thrombus-forming ability is required in vascular lesions in order to prevent hemorrhaging at these sites.

In accordance with the state of the art, attempts are made to counteract any life-threatening hemorrhages which may possibly occur in association with anticoagulant therapy, or anticoagulant therapy combined with lytic therapy, by breaking off the therapy and by administering coagulation promoters (antidotes). Such coagulation promoters contain factor VIII (FVIII) or substances which increase the endogenous concentration of FVIII in the blood such as desmopressin (DDAVP) (Mannucci P. M., Ruggeri Z. M., Pareti F. l., Capitano A., 1977, Lancet, 1, 869–872; EP 0 367 713 B1, 1992; U.S. Pat. No. 5,204,323, 1993), or an antifibrinolytic agent such as aprotinin, mixed together with desmopressin, tranexamic acid, ε-aminocaproic acid and 4-aminomethylbenzoic acid (WO 9220361, 1992). Other coagulation promoters are composed, inter alia, of coagulation factors, some of which have already been activated, as in the commercial product FEIBA® (Immuno AG), or of a prothrombin concentrate, as in the commercial product Beriplex® (Behringwerke A.G.) or in the commercial product Autoplex® (Baxter Inc.). All these antidotes principally bring about a reduction in the therapeutic effects of the active compounds and consequently also a reduction in the side effects due to these compounds. However, the effects due to the above-mentioned antidotes involve the danger that the preceding therapeutic result (the anticoagulation) is nullified, with a serious risk of thrombosis as a consequence.

In clinical practice, the activated partial thromboplastin time (aPTT) is used as a quantitative measure of the anticoagulant and fibrinolytic effect, with the bleeding time (BT) being a measure of the hemorrhagic tendency. A method of determining the bleeding time, which is also very reproducible in humans in clinical practice, is that of measuring the cutaneous bleeding time by the Simplate method (Lethagen S. and Kling S., 1993, Thrombosis Haemostasis 70, 595–597). In general, aPTT and BT correlate quite well with each other in the sense that an increased effect, as measured in increased aPTT values, also draws increased side effects, i.e. longer bleeding times, in its wake.

Mechanistic investigations on the course of hemostasis following a vascular lesion indicate that, in the phase of primary hemostasis, the blood platelets are mainly bound to subendothelial collagen fibers by means of the von Willebrand factor (vWF). vWF is the only factor which is able to efficiently bind to the exposed collagen both at low (e.g. in the venous region) and at high (e.g. in the arterial, coronary region or in association with plaque-determined vascular stenoses) shearing rates (Ruggeri Z. M., Seminars in Hematology, 1994, 31, 229–239). Subsequent platelet aggregation, and retraction and contraction of the aggregated platelets due to the involvement of thrombin, results, during secondary hemostasis, in the formation of a hemostatic occlusion (Hemker H. C. and Poliwoda H., 1993, 1–18, Barthels M. and Polidowa H., editors Thieme Verlag, Stuttgart, Germany).

vWF is the largest soluble plasma protein known to date. It is a multimeric glycoprotein which has two biological properties. It mediates platelet adhesion, with subsequent formation of a thrombus, in association with local vascular lesions, and it serves as a carrier for the procoagulatory coagulation factor VIII (Ruggeri Z. M. 1993 Current Opinion in Cell Biology, 5, 898–906). A certain amount of vWF is present in the subendothelium, and vWF is also stored, in factor VIII-free form, in the α granula of the blood platelets. Blood platelets possess two receptors for vWF: 1. GPI b in the GP Ib-IX-V complex and 2. GP IIb–IIIa (Ruggeri Z. M., 1994 Seminars in Hematology 31, 229–239). By way of the former receptor, vWF mediates adhesion of the platelets at the site of the vascular lesion and then supports the subsequent aggregation of the platelets by way of the GP IIb–IIIa receptor, although this aggregation is in the main sustained by the binding of fibrinogen to the GP IIb–IIIa receptor. Against this background, a discussion is in progress in the literature with regard to the principle of using inhibitors of vWF binding as anticoagulants (Alevriadou B. R., Moake J. L., Turner N. A., Ruggeri Z. M., Folie B. J., Phillips M. D., Schreiber A. B., Hrinda M. E., McIntire I. V., 1993, Blood, 81, 1263–1276; Gralnick H. R., Williams S., McKeown L., Kramer W., Krutzsch H., Gorecki M., Pinet A., Garfinkel L. I., 1992, Proc. Natl. Acad. Sci. USA, 89, 7880–7884).

It has been found, surprisingly, that while the additional administration of plasma vWF to pigs which are undergoing an anticoagulatory therapy protocol using r-hirudin, for example, did not impair the systemic anticoagulatory effect (aPTT), the bleeding side effect (BT) decreased to a level which was less than twice the bleeding time prolongation and then remained constant. In a control experiment without vWF infusion, the BT had risen to a value which was approximately 3 times that of the normal bleeding time (FIG. 1).

Figure 1:
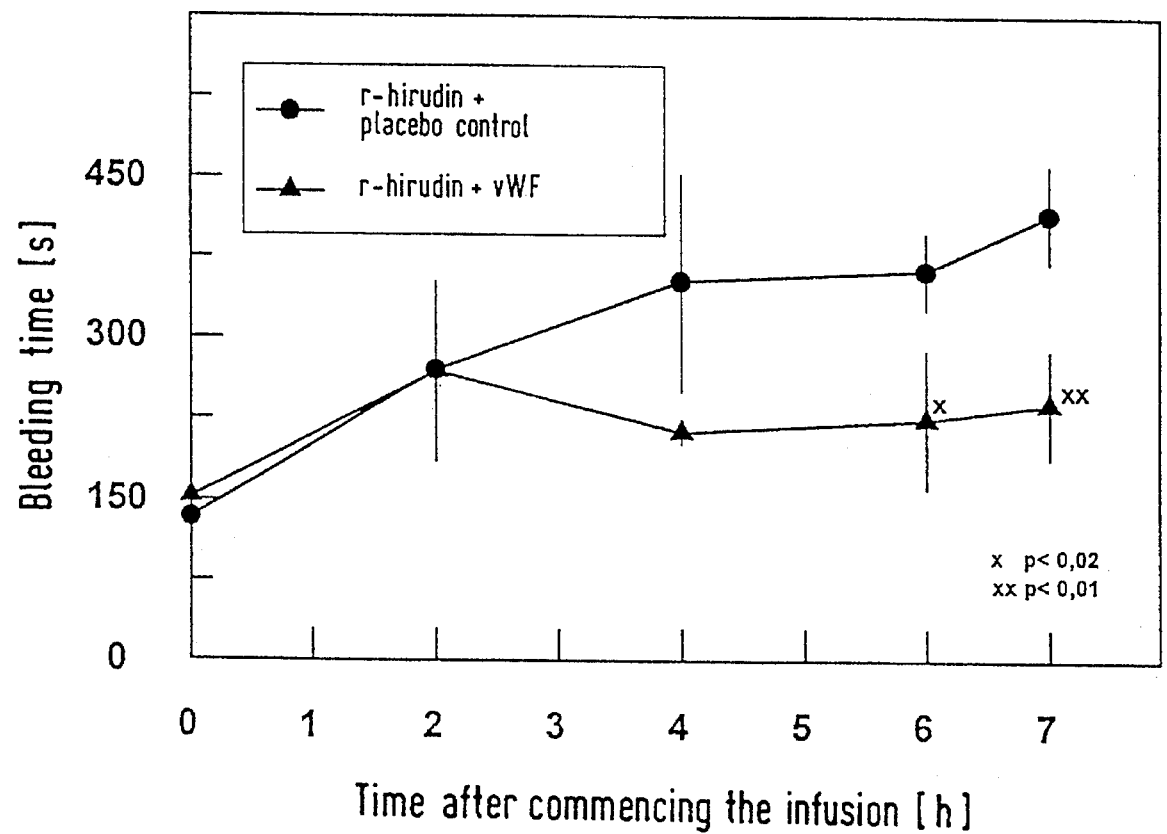
FIG. 1: Effect of vWF on the r-hirudin-induced cutaneous bleeding time in the pig: 0.3 mg/kg×h r-hirudin (placebo group, ●); 0.3 mg/kg×h r-hirudin plus, after 3 hours, 66 vWF units/kg, as an i.v. bolus, and 187 vWF units/kg×h, as an i.v. infusion of vWF (vWF group, Δ)

Consequently, the object of the invention is achieved by means of a process in association with anticoagulatory therapy and, where appropriate, in combination with fibrinolytic therapy, which process, by means of appropriate supplementation with a vWF-containing solution, brings about a separation of the above-described correlation between the desirable effect (indicated by the aPTT) and the undesirable side effect of bleeding (indicated by the BT): the therapeutic effect is retained, i.e. while the risk of a thrombosis is excluded, the side effects which are elicited by the effect of the anticoagulants or fibrinolytics are minimized.

The invention therefore relates to the use of vWF for preparing an agent which acts as a pseudoantidote in association with hemorrhages which are produced by administering antithrombotic and/or fibrinolytic agents. In addition, the invention relates to pharmaceutical compositions which contain an antithrombotic agent and/or a fibrinolytic agent as component A and contain vWF or fragments having vWF activity as component B.

The vWF concentrate which is employed can, for example, be the commercial product Haemate® HS (Behringwerke A.G.), which contains FVIII in addition to vWF.

EXAMPLE 1

Course of the bleeding time and of the aPTT following hirudin infusion and following confusion of a vWF solution (Haemate® HS equivalent to Haemate P®).

A total of 7 castrated male pigs were given a 7-hour intravenous infusion of 0.3 mg of recombinant hirudin (r-hirudin)/kg×h. Three hours after the infusion had commenced, 3 of the animals were additionally given an i.v. bolus of a vWF-containing concentrate (66 vWF units/kg) followed by a two-hour infusion of 187 vWF units/kg×h (vWF group). The other four animals were given a corresponding volume of sodium chloride solution in place of the vWF (placebo group). During the experiment, the cutaneous bleeding time was determined using the Simplate® method (Organon-Teknika), and the aPTT was measured in plasma in accordance with the Neothromtin® method (Behringwerke A.G.). As FIG. 1 shows, the bleeding time initially rises in both groups and, after 7 hours, has risen in the placebo group to approximately 3 times the normal value. In the vWF group, the bleeding time decreases following the treatment with vWF and has almost reached the normal value once again after 7 hours (the differences between the two groups at 6 and 7 hours are statistically significant). Consequently, vWF is able to renormalize the risk of a hemorrhage, which has been increased by administering the thrombin inhibitor r-hirudin.

The aPTT was measured in the same experiment as an indication of the anticoagulatory activity of r-hirudin. As Tab. 1 shows, no significant difference could be detected between the placebo group and the vWF group; an approximately 2-fold increase in the aPTT was observed in both groups.

TABLE 1

| Time after commencing the infusion [h] | aPTT [s] | |
| --- | --- | --- |
| | Placebo group | vWF group |
| 0 | 124.3 ± 56.0 | 101.0 ± 34.3 |
| 6 | 185.7 ± 103.2 | 213.7 ± 80.8 |
| 7 | 165.0 ± 83.7 | 214.8 ± 32.3 |

The following anticoagulants can be combined with the vWF: heparin; LMW heparin; synthetic (recombinant) thrombin inhibitors such as r-hir, and their derivatives such as polyethylene glycol hirudin or Hirulog; synthetic low molecular weight thrombin inhibitors such as Argartroban (MCI 9098, see Tamao Y. et al. loc cit; synthetic or recombinant FXa inhibitors such as TAP; synthetic or recombinant FVII inhibitors such as tissue factor pathway inhibitor (TFPI); blood platelet antagonists such as acetylsalicylic acid or synthetic fibrinogen receptor inhibitors and thrombocyte antibodies (e.g. 7E3); vitamin K antagonists such as warfarin, phenprocoumon and acenocoumarol.

The following fibrinolytics are very suitable for being combined with the abovementioned anticoagulants and vWF: streptokinase; plasminogen activators (rt-PA and uPA) and their derivatives such as, for example, APSAC.

EXAMPLE 2

Effect of a vWF solution (Haemate®) on bleeding time when associated with a combination of hirudin and aspirin.

In this experiment, the thrombin inhibitor hirudin was combined with the blood platelet inhibitor aspirin using a total of 4 pigs. Aspirin was first infused for half an hour at a concentration of 20 mg/kg and hirudin was then infused (t=0) for 7 hours at a concentration of 0.3 mg/kg×h.

After 3 hours, 2 of the animals were given vWF solution (Haemate® HS), specifically 66 vWF units/kg as an i.v. bolus and then a 2-hour i.v. infusion of 187 vWF units/kg×h. The remaining animals were given a corresponding quantity of sodium chloride solution. Table 2 shows that the bleeding time had risen to approximately 2.5 times the original value (0 value) after 3 hours. While administration of the vWF solution led to a marked decrease in the bleeding time (down to 1.8 times the original value) after 6 hours, the bleeding time of the NaCl-treated animals had increased still further to 2.9 times the original value.

TABLE 2

Anticoagulation due to hirudin and aspirin: reduction of the bleeding time due to the vWF concentrate

| Treatment | Bleeding time (multiple of the 0 value) | | |
|---|---|---|---|
| | 0 value | 3 hours | 6 hours |
| Anticoagulation (hirudin + aspirin + NaCl) | 1 | 2.5 ± 0.4 | 2.9 ± 0.4 |
| Anticoagulation (hirudin + aspirin + vWF)* | | | 1.8 ± 0.5 |

*Haemate ® HS

EXAMPLE 3

Since the vWF solution (Haemate® HS) which was used also contained the coagulation factor VIII (F VIII) in addition to vWF, tests were carried out to determine whether administration of a vWF concentrate which was low in F VIII could also be used to reduce the prolongation in bleeding time which is induced by r-hirudin. 7 pigs were infused with 0.3 mg of r-hirudin/kg×h for 7 hours. After 3 hours, 3 of the pigs were treated with vWF concentrate which was low in F VIII (66 vWF units/kg as an i.v. bolus, followed by 187 vWF units/kg×h as an i.v. infusion). 4 pigs were given the corresponding quantity of sodium chloride solution. Tab. 3 shows that the F VIII-low vWF concentrate also reduces the bleeding time which has been increased by r-hirudin.

TABLE 3

Effect of a vWF concentrate which is low in factor VIII on the cutaneous bleeding time which is induced by r-hirudin

| Treatment | Bleeding time (multiple of the 0 value) | | |
|---|---|---|---|
| | 0 value | 3 hours | 6 hours |
| r-hirudin + NaCl | 1 | 2.6 ± 1.0 | 2.9 ± 0.75 |
| r-hirudin + vWF | | | 1.9 ± 0.5 |

We claim:
1. A method for decreasing the bleeding side effect in a patient caused by administering anticoagulant and/or fibrinolytic agents comprising administering to said patient a therapeutically active amount of von Willibrand Factor, or a fragment having von Willibrand Factor activity.
2. The method according to claim 1, wherein in addition to said von Willibrand Factor, or a fragment having von Willibrand Factor activity, an antithrombotic agent and/or fibrinolytic agent is administered.

* * * * *